United States Patent [19]

Darougar

[11] Patent Number: 5,147,647
[45] Date of Patent: Sep. 15, 1992

[54] OCULAR INSERT FOR THE FORNIX

[76] Inventor: Sohrab Darougar, 2 Digby Place, Croydon CR0 5QR, England

[21] Appl. No.: 626,001

[22] Filed: Dec. 12, 1990

Related U.S. Application Data

[63] Continuation-in-part of Ser. No. 500,093, Mar. 21, 1990, which is a continuation of Ser. No. 330,959, Mar. 29, 1989, abandoned, which is a continuation of Ser. No. 104,045, Oct. 1, 1987, abandoned.

[51] Int. Cl.⁵ .............................................. A61F 9/00
[52] U.S. Cl. .................................... 424/427; 424/428
[58] Field of Search ........................ 424/427, 428, 429

[56] References Cited

U.S. PATENT DOCUMENTS

| | | | |
|---|---|---|---|
| 3,828,777 | 8/1974 | Ness | 424/427 |
| 3,995,635 | 12/1976 | Higuchi et al. | 424/427 |
| 4,014,335 | 3/1977 | Arnold | 424/427 |
| 4,034,758 | 7/1977 | Theeuwes | 424/427 |
| 4,135,514 | 1/1979 | Zaffaroni et al. | 424/427 |
| 4,164,559 | 8/1979 | Miyata et al. | 424/428 |
| 4,524,776 | 6/1985 | Withers et al. | 424/427 |

Primary Examiner—Thurman K. Page
Assistant Examiner—Amy Hulina
Attorney, Agent, or Firm—Nies, Kurz, Bergert & Tamburro

[57] ABSTRACT

A flexible ocular insert device adapted for the controlled sustained release of an ophthalmic drug into the eye, wherein the device includes an elongated cylindrical shaped body having a length of at least 8 mm and with the diameter of its body portion not exceeding 1.9 mm. The sustained release mechanism may be by diffusion or by osmosis or bioerosion. The insert device is advantageously inserted into the upper or lower fornix of the eye so as to be independent of movement of the eye by virtue of the fornix anatomy. In one embodiment of the invention, an insert device having a length of 8 to 25 mm, to suit eyes of different sizes, was employed for use in the lower fornix and a device having a length of 8 to 35 mm was employed for use in the upper fornix. The present insert device is of a size and configuration such that, upon insertion into the upper or lower fornix, the device remains out of the field of vision so as to be well retained in place and imperceptible by a patient over a prolonged period of use. Thus the device can be retained in the upper or lower fornix for 7 to 14 days or longer.

9 Claims, 3 Drawing Sheets

OCULAR INSERT FOR THE FORNIX

BACKGROUND OF THE INVENTION

This is a continuation-in part of application Ser. No. 500,093 filed Mar. 21, 1990, which is a continuation of application Ser. No. 330,959 filed Mar. 29, 1989 which is a continuation of application Ser. No. 104,045 filed Oct. 1, 1987.

This invention is concerned with improvements in or relating to ocular insert devices.

Various diseases of the eye are commonly treated by periodically applying ophthalmic drugs for example in the form of eye drops or ointment. While this is suitable and convenient in some cases, it can be a serious disadvantage that the drug is not dispersed in a continuous manner. With a view to overcoming this disadvantage it has been previously proposed, for example, in U.S. Pat. No. 3,416,530 of R.A. Ness assigned to Alza Corporation and subsequent patents of Alza Corporation to provide a flexible ocular insert device adapted for the controlled sustained release of the drug.

In for example U.S. Pat. No. 3,828,777 of R.A. Ness assigned to Alza Corporation it is stated that the ocular insert can be fabricated in any convenient shape for comfortable retention in the conjunctival sac of the eye and that the marginal outline can be ellipsoid, doughnut-shape, bean-shape, banana-shape, circular or rectangular; and in cross section it can be doubly convex, concavoconvex, or rectangular. It is suggested however that the original cross-sectional shape of the device is not of controlling importance. However, these previously proposed devices have in practice met with no more than limited success because most of the proposed shapes and sizes were not suitable for placement in the narrow upper and lower fornices. Also previous devices have tended not to remain in place in the eye and have at times caused irritation to the patient during use.

U.S. Pat. No. 4,186,184 to A. Zaffaroni discloses that the length of an insert device should be from 2 to 20 mm, its width 1 to 15 mm and its thickness 0.1 to 4 mm. A wide variety of shapes are disclosed, including ellipsoid, doughnut, bean, banana and square shapes.

U.S. Pat. No. 3,828,777 to Ness discloses an ocular device which is inserted in that portion of the eye bounded by the surface of the bulbar conjunctiva of the sclera of the eyeball and the palpebral conjunctiva of the lid. Such placement of the device would, however, be subject to eye movement and would not provide an anchored position such as is obtained in the present invention. Movement of the device causes pain, irritation, foreign body sensation and watering.

U.S. Pat. No. 4,343,787 to Katz discloses water soluble inserts for the eye in which broad dimensional ranges of sizes and shapes are employed. There is no description of an insert of a specific size and shape to allow it to be retained in the fornix portion of the eye.

U.S. Pat. No. 4,135,514 to Zaffaroni et al. relates to osmotic drug delivery devices which can be used for the administration of ocular drugs. A wide variety of shapes and sizes is disclosed.

EP-A-O 033 042 to Merck and Co., Inc. discloses ocular inserts which can take any of a variety of shapes, one of which may be an extruded rod. There is no description, however, of a device having dimensions which make it suitable for insertion into the fornix so as to be retained therein for 7 days or longer.

U.S. Pat. No. 4,730,013 to Bondi et al. discloses ocular inserts intended to overcome the problem of blurred vision arising from the use of particular insert materials. The maximum length of 5 mm employed by Bondi et al. is considerably smaller than the range of dimensions employed in the present invention. It is shown in the present invention that a device with a length of 5 mm falls well below the minimum length required for retention in the eye of humans for 7 days or more.

EPO 0 251 680 to IOLAB, Inc. discloses a device for controlled drug release to the eye, in which an external matrix rapidly soluble in body fluids and having bioerodible microparticles containing the drug are positioned in the upper or lower conjunctival cul-de-sac of the eye. There is no description of a device which is retained in the eye for seven days or longer, or of the specific shape and dimension of the device of the invention for placement in the upper or lower fornix.

U.S. Pat. No. 3,845,201 to Haddad et al. discloses an ocular device for insertion in the cul-de-sac of the conjunctiva. The device may be any of various shapes, preferably disc shaped.

U.S. Pat. No. 4,164,559 to Miyata et al. discloses a soluble device for drug delivery to the eye including a collagen insert having an ovoid shape. The device is described as insertable into the inferior fornix. There is no description of a device having the dimensions employed in the present invention for retention of seven days or longer.

U.S. Pat. No. 4,179,497 to Cohen et al. discloses water soluble inserts of various shapes for applying drugs to the cul-de-sac of the conjunctiva. Again there is no description of an insert having the specific dimensions of the invention.

Other ocular inserts are described in the following literature reports Urtti et al. (1990) Controlled drug delivery devices for experimental ocular studies with timolol.1.In vitro release studies. *Int. J. Pharm.*, 61, 235-240; and Urtti et al (1990) Controlled drug delivery devices for experimental ocular studies with timolol.-2.Ocular and systemic absorption in rabbits. *Int. J. Pharm.* 61, 241-249. These reports describe the use of a permeable hollow tube (silicone) for ocular delivery. The tube has a diameter of 1.94 mm which is outside the dimensions employed in the present invention. Also, the device was only observed in the eye for an 8 hour period.

SUMMARY OF THE INVENTION

It is an object of the present invention to provide an improved ocular insert device adapted for the controlled sustained release of a drug. The present invention is sometimes referred herein as a sustained drug release device or SDRD.

It has been found, in accordance with the present invention, that a flexible ocular insert device having a body of a thin elongated circular cylindrical configuration of specific dimensions is well retained in place and tolerated by the patient over a prolonged period of se for example up to 7 to 14 days or longer. The device may be inserted in the upper or lower fornix of the conjunctiva between the sclera of the eyeball and the upper or lower eyelid, being held in position preferably in the extreme outer end portion of the upper or lower fornix and prevented from moving downward or upward respectively by the pressure of the lid against the eyeball. This position of the ocular insert of the present invention in the upper or lower fornix is shown in detail in the drawings as described hereinafter.

In particular, the device is advantageously inserted so as to fit within the upper or lower fornix by restriction of the cross sectional dimensions of the device to allow it to slip into this position and then with a length requirement that provides for anchoring the device across the lid. By locating the device within the fornix, the device is imperceptible to the patient, through restriction of the device to a specific size range and shape, with the upper limit not being governed by the geometric space limitation of the whole eye, and by placement specifically within the fornix, not simply within the conjunctival cul-de-sac. In addition, the retention of the present insert device is independent of the movement of the eye by virtue of the fornix anatomy. In contrast, a device placed anywhere on the bulbar conjuctiva would be subject to eye movement and cause discomfort to the patient.

The insert device of the present invention must be positioned precisely and remain anchored in the upper or lower fornix, known also as the superior conjunctival fornix or the inferior conjunctival fornix, as distinct from the positioning of other kinds of devices anywhere in the conjunctival cul-de-sac. The device of the present invention must be flexible to allow it to bend along the curvature of the eye within the fornix. In particular, such flexibility must be sufficient to allow it to bend along the curvature of the eye within the upper or lower fornix upon being positioned so that the longitudinal axis of the device is generally parallel to the transverse diameter of the eyeball.

The present insert device is imperceptible by the patient when anchored properly in the fornix, whereas prior art devices are perceived as foreign bodies. Upon proper positioning in the fornix, the present insert device is independent of eye movement and does not move when the eye moves. The device of the present invention also remains out of the field of vision. In addition, it can be placed and held in position without interference during surgical procedures.

The length of the present insert device is also critical to the anchoring process in the fornix. The length of the device is related to the size of the eye, hence the optimum length for the human adult is 25 mm, for children is about 15 to 18 mm and for newborn babies is 8 mm in length.

In general, for adults, the lengths of the upper fornix and lower fornix are about 45 to 50 mm and 35 to 40 mm respectively. Thus an insert device of the present invention with a length of up to 35 mm may remain in the upper fornix and one with a length of up to 25 mm may remain in the lower fornix without causing discomfort.

The invention provides, in one of its aspects, a flexible ocular insert device adapted for the controlled sustained release of an ophthalmic drug into the eye, characterized in that the device comprises a body having a thin elongated circular cylindrical configuration, the device having a length of at least 8 mm and a diameter not exceeding 1.9 mm. Advantageously the dimensions of the device according to the invention are selected as: a length of 8 to 25 mm for use in the lower fornix and a length of 8 to 35 mm for use in the upper fornix; and a diameter of 0.5 to 1.9 mm.

The circular cylindrical body terminates at transverse end surfaces which may for example be planar or domed.

The material of the insert device is for example a synthetic polymer.

The present invention provides a flexible ocular insert device adapted for the controlled sustained release of an ophthalmic drug into the eye, characterized in that the device comprises a body having a circular, cylindrical configuration; the length of the device is at least 8 mm and the diameter of its body does not exceed 1.9 mm.

Examples of ophthalmic drugs include antibiotics such as tetracycline, chlortetracycline, bacitracin, neomycin, polymyxin, gramicidin, cephalexin, oxytetracycline, chloramphenicol kanamycin, rifampicin, gentamycin, erythromycin and penicillin; anibacterials such as sulfonamides, sulfadiazine, sulfacetamide, sulfamethiazole and sulfisoxazole, nitrofurazone and sodium propionate; antivirals including idoxuridine, trifluorothymidine, acyclovir, ganciclovir and interferon; antiallergenics such as sodium cromoglycate, antazoline, methapyriline, chlorpheniramine, cetirizine and prophenpyridadine; anti-inflammatories such as hydrocortisone, hydrocortisone acetate, dexamethasone, dexamethasone 21-phosphate, fluocinolone, medrysone, prednisolone acetate, fluoromethalone, betamethasone, and triaminolone; decongestants such as phenylephrine, naphazoline and tetrahydrozoline: miotics and anticholinesterase such as pilocarpine, acetylcholine chloride, physostigmine, eserine, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; immunological drugs such as vaccines and immune stimulants; hormonal agents such as estrogens, estradiol, progestational, progesterone, insulin, calcitonin, parathyroid hormone and peptide, vasopressin, hypothalamus releasing factor; beta adrenergic blockers such as timolol maleate, levobunolol HCl and betaxolol HCl; growth factors such as epidermal growth factor and fibronectin; carbonic anhydrase inhibitors such as dichlorphenamide, acetazolamide and methazolamide and other drugs such as prostaglandins, antiprostaglandins, and prostaglandin precursors.

The drugs may be used in conjunction with a pharmaceutically acceptable carrier. Examples of pharmaceutically acceptable carriers include solids such as starch, gelatin, sugars, e.g., glucose, natural gums, e.g., acacia, sodium alginate, carboxy-methyl cellulose, polymers, e.g., silicone rubber; liquids such as sterile water, saline, dextrose, dextrose in water or saline; condensation products of castor oil and ethylene oxide liquid glyceryl triester of a lower molecular weight fatty acid; lower alkanols; oils such as corn oil, peanut oil, sesame oil, and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxy-methylcellulose, sodium alginate, poly(vinylpyrolidone), alone, or with suitable dispensing agents such as lecithin, polyoxyethylene stearate. The carrier may also contain adjuvants such as preserving, stabilizing, wetting or emulsifying agents.

The mechanism of controlled sustained drug release into the eye is for example diffusion, osmosis or bio-erosion and these mechanisms are described for example in U.S. Pat. No. 4,186,184 and in "Therapeutic Systems" by Klaus Heilmann published by Georg Thieme, Stuttgart 1978.

The period of controlled sustained release is for example up to 7 to 14 days or longer.

In one exemplary embodiment of the present invention utilizing the diffusion mechanism the configuration of the insert device is tubular with its cylindrical wall closed by transverse end walls to define a reservoir for the drug which is in liquid or gel form. At least the cylindrical wall is a membrane permeable by diffusion so that the drug is released continuously at a controlled rate through the membrane into the tear fluid.

In one exemplary embodiment of the invention utilizing the osmosis mechanism, the configuration of the insert device is tubular with domed end walls, and the device comprises a transverse impermeable elastic membrane dividing the tubular interior of the device into a first compartment and a second compartment; the first compartment is bounded by a semi-permeable membrane and the impermeable elastic membrane, and the second compartment is bounded by an impermeable material and the elastic membrane. There is a drug release aperture in the impermeable end wall of the device.

The first compartment contains a solute which cannot pass through the semi-permeable membrane and the second compartment provides a reservoir for the drug which again is in liquid or gel form.

When the device is placed in the aqueous environment of the eye water diffuses into the first compartment and stretches the elastic membrane to expand the first compartment and contract the second compartment so that the drug is forced through the drug release aperture.

In one exemplary embodiment of the invention utilizing the bioerosion mechanism, the configuration of the insert device is rod-like being constituted from a matrix of bioerodible material in which the drug is dispersed. Contact of the device with tear fluid results in controlled sustained release of the drug by bioerosion of the matrix. The drug may be dispersed uniformly throughout the matrix but it is believed a more controlled release is obtained if the drug is superficially concentrated in the matrix.

In another embodiment of the invention, there is employed a solid non-erodible rod with pores and dispersed drug. The release of drug can take place via diffusion through the pores. Controlled release can be further regulated by gradual dissolution of solid dispersed drug within this matrix as a result of inward diffusion of aqueous solutions.

Examples of the materials for a permeable membrane for the diffusion mechanism include insoluble microporous materials of polycarbonates, polyvinyl chlorides, polyamides, copolymers of polyvinyl chloride and acrylonitrile, polysulphones, polyvinylidene fluorides, polyvinyl fluorides, polychloroethers, polyformaldehydes, acrylic resins, polyurethanes, polyimides, polybenzimadozoles, polyvinyl acetates, polyethers, cellulose esters, porous rubbers, cross-linked poly(ethylene oxide), cross- linked polyvinyl pyrrolidone, cross-linked poly(vinyl alcohol) and polystyrenes.

The drug in liquid or gel form for the diffusion mechanism comprises a diffusion medium which also serves as a pharmaceutical carrier and in which the active ingredient of the drug is dissolved or suspended; the active ingredient is preferably of no more than limited solubility in the medium. Examples of diffusion media include saline, glycrin, ethylene glycol, propylene glycol, water (which may also contain emulsifying and suspending agents), mixtures of propylene glycol monostearate and oils, gum tragacanth, sodium alginate, poly(vinyl pyrrolidone), polyoxyethylene stearate, fatty acids and silicone oil.

Examples of materials for an osmotic semi-permeable membrane include cellulose acetate and its derivatives, partial and completely hydrolyzed ethylene-vinyl acetate copolymers, highly plasticized polyvinyl chloride, homo- and copolymers of polyvinyl acetate, polyesters of acrylic acid and methacrylic acid, polyvinyl alkyl ethers, polyvinyl fluoride; silicone polycarbonates, aromatic nitrogen-containing polymeric membranes, polymeric epoxides, copolymers of an alkylene oxide and alkyl glycidyl ether, polyurethanes, polyglycolic or polyacetic acid and derivatives thereof, derivatives of polystyrene such as poly(sodium styrenesulfonate) and poly(vinyl benzyltrimethyl-ammonium chloride), ethylene-vinyl acetate copolymers.

Examples of solutes which cannot pass through the semi-permeable membrane in an osmotic mechanism include water-soluble inorganic and organic salts and compounds such as magnesium sulfate, magnesium chloride, sodium chloride, lithium chloride, potassium sulfate, sodium carbonate, sodium sulfate, lithium sulfate, calcium bicarbonate, sodium sulfate, calcium sulfate, potassium acid phosphate, calcium lacetate, magnesium succinate, tartaric acid, acetamide, choline chloride, soluble carbohydrates such as sorbitol, mannitol, raffinose, glucose, sucrose and lactose.

Examples of bioerodible matrix materials include polyesters of the general formula —O—(W)—CO— and mixture thereof, wherein W is a lower alkylene of 1 to 7 carbons and may include a member selected from the group of alkylenes of the formula —$CH_2$—, or —CH—$CH_2$—, and Y has a value such that the molecular weight of the polymer is from about 4,000 to 100,000. The polymers are polymerization-condensation products of monobasic hydroxy acid of the formula $C_nH_{2n}$ (OH)COOH wherein n has a value of 1 to 7, preferably 1 or 2 and the acid is especially lactic acid or glycolic acid. Also included are copolymers derived from mixtures of these acids. Bioerodible materials also include poly(orthoesters). These materials have the following general formula:

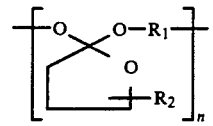

wherein $R_1$ is an alkylene of 4 to 12 carbons, a cycloalkylene of 5 to 6 carbons substituted with an alkylene of 1 to 7 carbons and an alkyleneoxy of 1 to 7 carbons, and $R_2$ is a lower alkyl of 1 to 7 carbons.

Other bioerodible matrix materials which may be employed include: (1) Polyanhydrides such as poly(p-carboxyphenoxy) alkyl (e.g. p-carboxyphenoxypropane) or polymeric fatty acid dimer (e.g. polydodecanedioic acid) compounds and further co-polymers with sebacic acid, or phthalic acid such as disclosed in Chasin et al., Polyanhdrides for Controlled Drug Delivery, *Biopharm.*, Feb. 1988, 33–46; and Lee et al. (1988), The Use of Bioerodible Polymers and 5 fluorouracil in Glaucoma Filtration Surgery, *Invest. Ophthalmol. Vis. Sci.*, 29, 1692–1697; (2) Poly (alkyl-2-cyanoacrylates) such as poly (hexyl-2-cyanoacrylate) as described by Douglas et al. (1987), Nanoparticles in Drug Delivery, *CRC Crit. Rev. Therap. Drug Carr. System.*, 3, 233-261; and (3) Polyamino acids such as copolymers of leucine and methyl glutamate.

Further information on membrane and bioerodible materials is contained in U.S. Pat. Nos. 3,828,777 and 4,186,184 and also the following references: Leong and Langer (1987), Polymeric Controlled Drug Delivery, *Adv. Drug Del. Rev.*, 1, 199-233; and Smith et al. (1990), Bioerodible Polymers for Delivery of Macromolecules, *Adv. Drug Del. Rev.*, 4, 343-357.

Examples of materials for use as non-erodible rods include polymers such as hydroxyethylmethacrylate and further co-polymers with methacrylic acid, methylmethacrylate, N-vinyl 2-pyrrolidone, allyl methacrylate, ethylene glycol dimethacrylate, ethylene dimethacrylate, or 1,1,1 trimethylopropane trimethacrylate, and dimethyl diphenyl methylvinyl polysiloxane.

The above and other aspects of the present invention will become more clear from the following description, to be read with reference to the accompanying drawings of devices embodying the invention. This description is given by way of example only, and not by the way of limitation of the invention.

DESCRIPTION OF THE PREFERRED EMBODIMENTS

Figure 1:
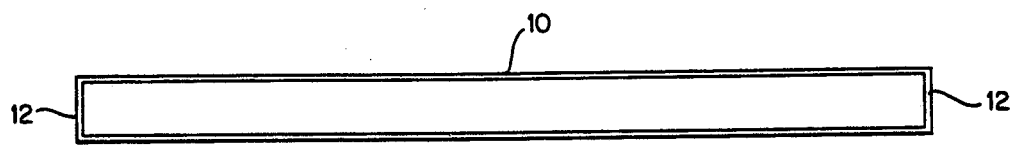
FIG. 1 shows a diagrammatic sectional view of a diffusional ocular insert device embodying the invention.

The ocular insert device shown in FIG. 1 comprises a circular cylindrical wall 10 of a microporous synthetic polymer membrane which is insoluble in tear fluid but is permeable by diffusion. The cylindrical wall 10 is closed by transverse planar end walls 12 which may be of the same microporous synthetic polymer membrane as the cylindrical wall 10 or alternatively may be impermeable. The overall length of the device is 8 to 25 mm or up to 35 mm for the upper fornix and its external diameter 0.5-1.9 mm.

The cylindrical wall 10 and the end walls 12 define a reservoir for a drug which diffuses through the membrane as described hereinbefore.

Figure 2:
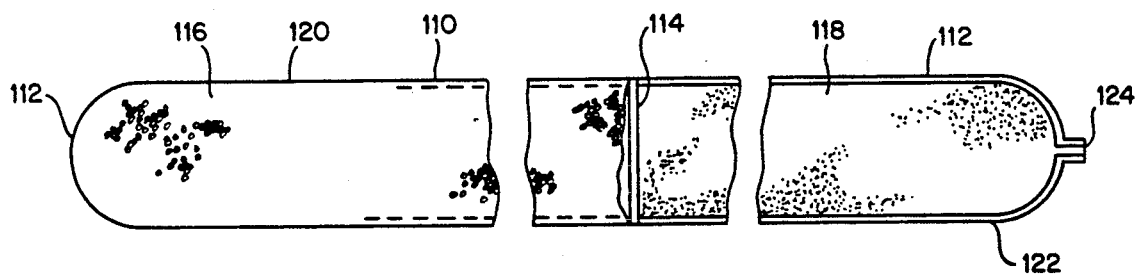
FIG. 2 shows a diagrammatic sectional view of an osmotic ocular insert device embodying the invention.

The ocular insert device shown in FIG. 2 comprises a circular cylindrical wall 110 closed by hemispherical domed end portions 112. The device also comprises, perpendicular to the axis of the cylindrical wall, an impermeable elastic membrane 114 dividing the interior of the device into a first compartment 116 and a second compartment 118. The cylindrical wall 110 comprises different materials as respectively do the end walls 112 so that the first compartment is bounded by a semipermeable synthetic polymer membrane 120 and the elastic membrane 114 and the second compartment is bounded by an impermeable synthetic polymeric membrane 122 and the elastic membrane 114. There is an axial drug release aperture 124 in the membrane 122 at the domed end portion 112 thereof.

The first compartment 116 contains a solute and the second compartment provides a reservoir for a drug which is forced through the aperture 124 by the stretching of the elastic membrane 114 under osmosis as described hereinbefore.

Figure 3:
FIG. 3 shows an enlarged diagrammatic sectional view of a bioerodible insert device embodying the invention.

The ocular insert device shown in FIG. 3 comprises a circular cylindrical body 210 with domed end portions 212. The device is constituted from a matrix of synthetic polymeric bioerodible material in which a drug is dispersed, being concentrated superficially of the matrix for controlled release therefrom as the matrix bioerodes.

The device having the configuration as shown in FIG. 3 may also be constituted of a solid non-erodible material having pores and dispersed drug as previously discussed.

The overall length and diameter of each of the devices of FIG. 2 and FIG. 3 is the same as for the device of FIG. 1.

The ocular insert device of the present invention may be installed in the fornix by the method as follows. The applicator consists of a tube with a length of about 35 mm and a flexible container with a capacity of about 500 microlitre containing a pharmaceutically acceptable viscous substance in the form of a cream:

(a) Insert the SDRD into the tube. Squeeze the container until the viscous substance pushes the SDRD into the mouth of the tube.

(b) Ask the patient to sit down and hold his/her chin slightly up.

(c) Ask the patient to look down continuously through the exercise.

(d) Separate the upper lid from the globe by about 4 to 5 mm by holding the lashes and gently pulling the lid forward and upward. Insert the tube under the eyelid for about 5 mm near the inner corner of the eye. Do not touch the inner corner of the eye and the globe.

(e) Push out the SDRD by squeezing the container gently and continuously. In the meantime move the tube slowly from the inner corner toward the outer corner, holding the tip of the tube at about 5 mm from the lid margin constantly. Stop about 5 mm from the outer corner.

N.B. By squeezing the container and moving the tube from one corner to another corner of the eye, the SDRD should come out of the tube and sit between the lid and globe near the upper fornix.

(f) Put tip of a finger at just about the end of the tube and hold the end of SDRD in position. Remove the tube.

(g) With the help of the tip of a finger, gently push the SDRD upward and toward the deep fornix. Repeat the movement twice more, once in the middle of the lid and once near the inner corner.

(h) Ask the patient to move the eye upward and downward three times. Make sure that the device is in position and is not coming out.

The device may also be installed directly by the patient using similar procedures as described above.

Figure 4:
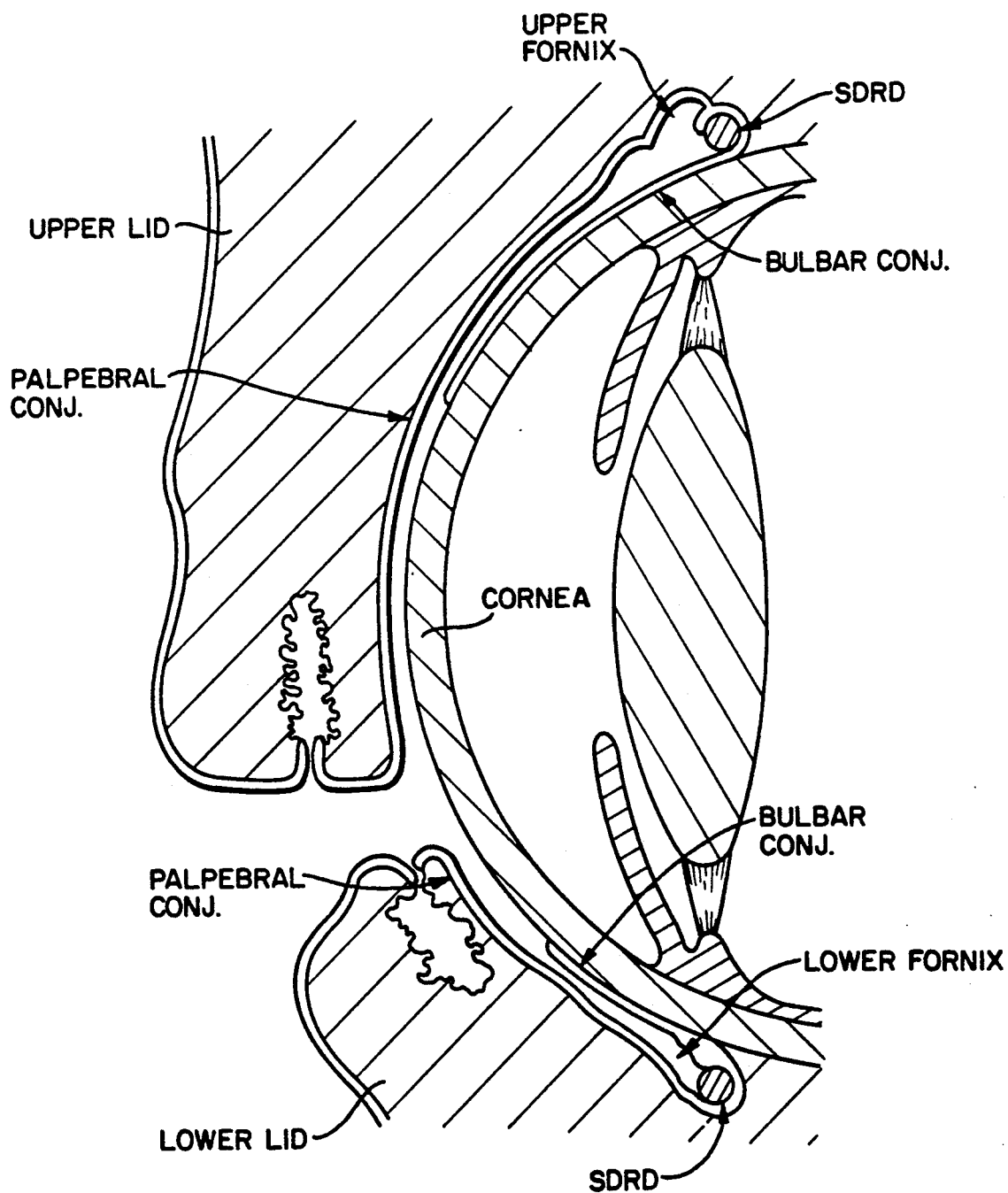
FIG. 4 shows a diagrammatic sectional view of the eye with an ocular insert device of the present invention installed in the upper and lower fornix.
Figure 5:
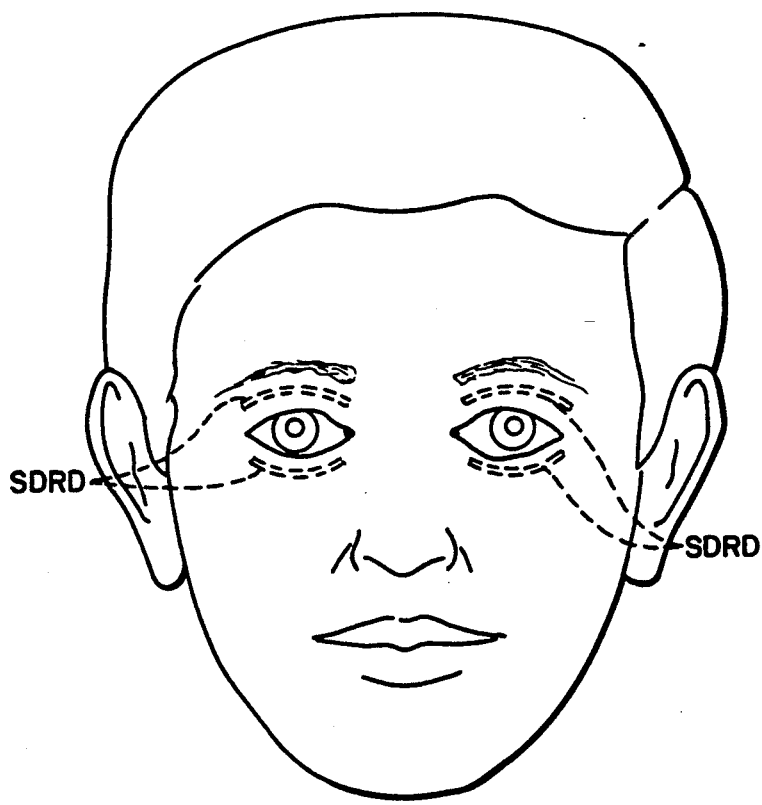
FIG. 5 shows a representation of the head of a patient with the location of the installed ocular insert device shown in dashed lines.
Figure 6:
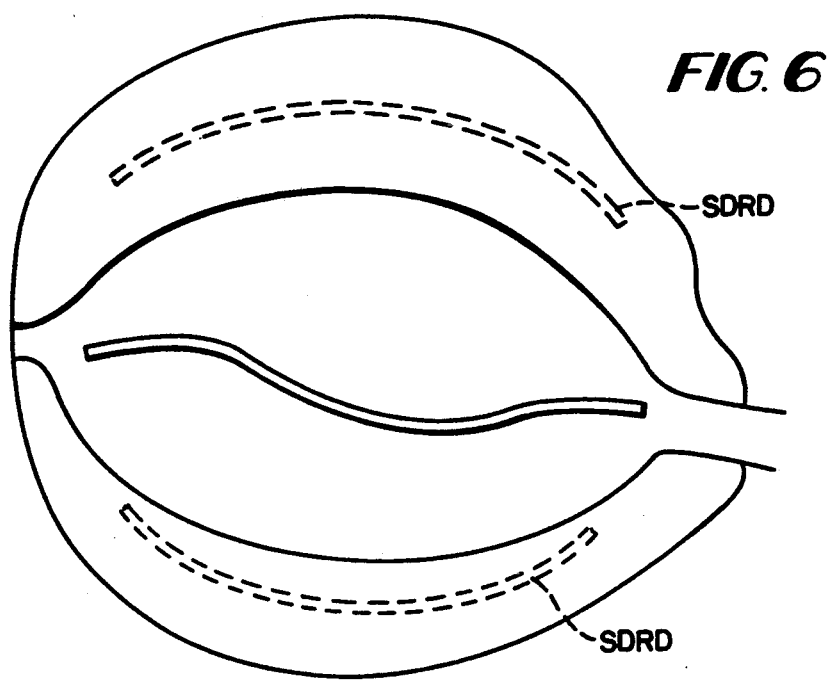
FIG. 6 shows the position of the installed ocular insert device in a closed eye.

Upon installation, tne ocular insert device of the present invention will be positioned in the upper or lower fornix in one of the positions as shown in FIGS. 4 through 6 of the drawings.

The following Table 1 shows the results obtained by the use of the ocular insert of the present invention in tests with human volunteers. As shown by the test results, when an insert device having the preferred dimensions was employed, the device was retained by the patient over a prolonged period of time without discomfort.

TABLE 1

Human Volunteers Summary

| Experiment | Size (mm) length × diameter | Site | Eye | Retention | Adverse Effects | Remarks |
|---|---|---|---|---|---|---|
| 1 | 10 × 2 | Lower fornix | Right | 7 days | Foreign body sensation | Moved to the upper fornix |
| 2 | 10 × 2 | Lower fornix | Left | 1 day | Foreign body sensation | Came out after rubbing the eye |
| 3 | 10 × 2 | Lower fornix | Left | 1 day | Nil | Came out |
| 4 | 10 × 2 | Upper fornix | Right | 1 day | Nil | Came out |
| 5 | 8 × 2 | Lower fornix | Right | 2 days | Nil | Came out |
| 6 | 10 × 2 | Lower fornix | Right | 5 days | Foreign body sensation | Came out when sleeping |
| 7 | 10 × 2 | Lower fornix | Left | 1 day | Foreign body sensation | Came out |
| 8 | 10 × 2 | Upper fornix | Right | 4 days | Foreign body sensation | After 1 day moved to the lower fornix |
| 9 | 10 × 2 | Upper fornix | Right | 5 days | Nil | Removed after 5 days |
| 10 | 8 × 2 | Upper fornix | Right | 2 days | Nil | Came out when sleeping |
| 11 | 8 × 2 | Upper fornix | Right | 3 days | Foreign body sensation | Considerable movement in the eye |
| 12 | 20 × 1 | Upper fornix | Left | 7 days | Nil | Removed after 7 days |
| 13 | 20 × 1 | Upper fornix | Left | 14 days | Nil | Removed after 14 days |
| 14 | 25 × 1.8 | Upper fornix | Left | 14 days | Nil | Removed after 14 days |
| 15 | 30 × 1.8 | Upper fornix | Left | 14 days | Nil | Removed after 14 days |
| 16 | 8 × .5  10 × .5 | Upper fornix | Left | 5 days | Nil | Removed after 5 days |
| 17 | 12 × .75  15 × .75  20 × 1 | Upper fornix | Left or Right | 7 to 14 days | Nil | Removed |
| 18 | 25 × 1.8 | Upper fornix | Left | 30 days | Nil | Device removed |
| 19 | 25 × 1.8 | Upper fornix | Right | 7 days | Nil | Device removed |
| 20 | 25 × 1.8 | Upper fornix | Right | 21 days | Nil | Device removed |
| 21 | 25 × 1.8 | Upper fornix | Left | 14 days | Nil | Device removed |

Notes:
(1) The ocular insert in all experiments was constructed of silicone rubber. In experiments Nos. 12 through 15 and 18 through 20, the material was in the form of a tube.
(2) Multiple patients were used in experiments Nos. 16 and 17.
(3) The patients in experiment No. 16 were newborn babies.
(4) The patients in experiment No. 17 were children ages 5 to 12 years.

By the way of comparison, ocular inserts having dimensions outside those of the present invention were constructed, with dimensions as follows:
Size: Approximately 12×5×1 mm
Shape: Oval, Lower surface with concave curvature, upper surface with convex curvature
Composition: Polypeptide matrix containing erythromycin estolate
Consistency: Semi-rigid These inserts outside the scope of the present invention were placed in the upper fornix of the right eye of 16 patients between ages of 6 and 8. The retention of the device in this location was followed over a period of 10 days. The right eye was examined twice a day for the presence of the insert. A new insert was replaced in the fornix if dislocation occurred. The results which were obtained showed that inserts of this type outside the scope of the present invention required frequent replacement into the eye over a ten day period. In no case were such inserts retained for more than 3 days at a time.

The foregoing comparative tests show the importance of employing an ocular insert device having the size and shape as described herein.

In the use of a prior art device known as Ocusert, the subject of U.S. Pat. No. 3,828,777 to Ness, the device is inserted into the conjunctival cul-de-sac. Either of two systems may be employed, with the Pilo-20 system measuring 5.7×3.4 mm on its axes and 0.3 mm in thickness and the Pilo-40 system measuring 5.5×13 mm on its axes and 0.5 mm in thickness. Various problems in retention and irritation which occurred in the use of this device are documented, for example, in the following publications: P. Sihvola et al., Practical problems in the use of Ocusert-pilocarpine delivery system, *Acta Ophthalmol.(Cooenh.)*, Dec. 1980, 58 (6), pp 933–937; S.E. Smith et al., Comparison of the pupillary, refractive and hypotensive effects of Ocusert-40 and pilocarpine eyedrops in the treatment of chronic simple glaucoma, *Br. J. Ophthalmol.*, Apr. 1979, 63(4) pp 228–232; and I.P. Pollack et al., The Ocusert pilocarpine system: advantages and disadvantages, *South Med. J.*, Oct. 1976, 69 (10), pp 1296–1298.

While the ocular insert of the present invention has been described herein as particularly well suited for treatment of humans, it is also within the scope of the invention to employ the present invention in the treatment of other animals such as cows and horses for diseases such as pink eye and the like.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method for the controlled sustained release of an ophthalmic drug into the eye over a period of time which comprises:

(a) inserting an elongated cylindrical shaped device of a polymeric material in the form of a rod or tube containing an ophthalmic drug into the upper or lower fornix so as to anchor said device into position therein, wherein the length of the device is at least 8 mm and the diameter does not exceed 1.9 mm, wherein said device is sufficiently flexible to allow it to bend along the curvature of the eye within the upper or lower fornix upon being positioned so that the longitudinal axis of said device is generally parallel to the transverse diameter of the eyeball, said device being of a size and configuration such that, upon insertion into the upper or lower fornix, the device does not extend onto any visible portion of the eyeball, said device being independent of movement of the eye and remaining out of the field of vision so as to be well retained in place and imperceptible by a patient over a prolonged period of use; and (b) allowing said device to remain in the upper or lower fornix for drug release during said period of time, whereby the device when inserted into the upper or lower fornix can be retained therein for more than seven days.

2. The method of claim 1 wherein the length of the device is from 8 to 25 mm for use in the lower fornix to suit the eyes of different sizes such as infants, children and adults.

3. The method of claim 1 wherein the length of the device is from 8 to 35 mm for use in the upper fornix to suit the eyes of different sizes such as infants, children and adults.

4. The method of claim 1 wherein the precise and optimum length of the device is correlated to the length of the individual fornix of the patient and size of the eye.

5. The method of claim 1 wherein the diameter of the device is from 0.5 to 1.9 mm to suit the eyes of different sizes such as infants, children and adults.

6. The method of claim 1 wherein the device is tubular and the mechanism of drug release is by diffusion through an outer wall of the device.

7. The method of claim 1 wherein the device is tubular and the mechanism of drug release is by osmosis.

8. The method of claim 1 wherein the device is in the shape of a rod and the mechanism of drug release is bioerosion.

9. The method of claim 1 wherein the body is a non-erodible rod and the mechanism of drug release is by diffusion including possible drug dissolution.

* * * * *

UNITED STATES PATENT AND TRADEMARK OFFICE
CERTIFICATE OF CORRECTION

PATENT NO. : 5,147,647
DATED : September 15, 1992
INVENTOR(S) : Sohrab Darougar

It is certified that error appears in the above-identified patent and that said Letters Patent is hereby corrected as shown below:

Column 2, line 60, cancel "se", insert --use--.

Column 5, line 67, cancel "glycrin", insert --glycerin--.

Column 6, line 26, cancel "lacetate", insert --lactate--.

Column 6, line 32, cancel "mixture", insert --mixtures--.

Column 9, line 39 and 40, the data should appear as follows:

9  10 X 2  Upper   Right  5 days  Nil  Removed
           fornix                       after 5
                                        days Column 10, line 44, cancel "3.4", insert --13.4--.

Signed and Sealed this

Eleventh Day of January, 1994

Attest:

BRUCE LEHMAN

Attesting Officer        Commissioner of Patents and Trademarks